United States Patent
Bruun-Jensen

[11] Patent Number: 5,723,096
[45] Date of Patent: Mar. 3, 1998

[54] APPARATUS FOR DISINFECTING CONTACT LENSES

[75] Inventor: Jørgen Bruun-Jensen, Slagelse, Denmark

[73] Assignee: Synoptik A/S, Rodovre, Denmark

[21] Appl. No.: 619,520

[22] PCT Filed: Oct. 27, 1994

[86] PCT No.: PCT/DK94/00394

§ 371 Date: Apr. 29, 1996

§ 102(e) Date: Apr. 29, 1996

[87] PCT Pub. No.: WO95/12141

PCT Pub. Date: May 4, 1995

[30] Foreign Application Priority Data

Oct. 29, 1993 [DK] Denmark .................. 1221/93

[51] Int. Cl.⁶ ........................................... A61L 2/18
[52] U.S. Cl. .................. 422/301; 422/30; 134/901; 206/5.1
[58] Field of Search ...................... 422/300, 301, 422/30; 134/901; 206/5.1

[56] References Cited

U.S. PATENT DOCUMENTS

| | | |
|---|---|---|
| 4,396,583 | 8/1983 | Le Boeuf ......................... 422/301 |
| 5,011,661 | 4/1991 | Schäfer et al. ................... 422/30 |
| 5,089,240 | 2/1992 | Perlaky ........................... 422/300 |
| 5,143,104 | 9/1992 | Iba et al. ......................... 134/901 |
| 5,196,174 | 3/1993 | Cerola et al. .................... 422/300 |
| 5,270,002 | 12/1993 | Neff, II et al. .................. 134/901 |

FOREIGN PATENT DOCUMENTS 368443  5/1990  European Pat. Off. .

*Primary Examiner*—Christopher Upton
*Attorney, Agent, or Firm*—Oblon, Spivak, McClelland, Maier & Neustadt, P.C.

[57] ABSTRACT

In an apparatus for disinfecting contact lenses (19, 20), said contact lenses are immersed in a reaction vessel (1) with a 3% $H_2O_2$-solution (21). The contact lenses (19, 20) are placed in a lens holder (13, 14) on a frame (6) which also comprises a catalyst (9) in a compartment (7), to which the $H_2O_2$-solution has access. The catalyst (9) neutralizes the $H_2O_2$-solution, but said neutralization is delayed at first by the developed oxygen being collected and maintained in contact with the surface of an apertured system of spokes (10; 10a to 10h) of the catalyst (9) in such a manner that the disinfecting effect is improved.

4 Claims, 2 Drawing Sheets

APPARATUS FOR DISINFECTING CONTACT LENSES

TECHNICAL FIELD

The invention relates to an apparatus of the type described in the preamble of claim 1.

BACKGROUND ART

Contact lenses must be disinfected by the user when they are removed from the eyes. The most well-known disinfecting system is based on hydrogen peroxide $H_2O_2$, which in the highly purified form and in acid environment is highly destructive to all microorganisms. The hydrogen peroxide can be neutralized into oxygen and water by means of either a catalyst system or an enzyme system in such a manner that the hydrogen peroxide is removed from the contact lenses before said lenses are to be used again.

The apparatus of the type stated in the preamble of claim 1 comprises as indicated in said preamble a catalyst system for decomposing or neutralizing the hydrogen peroxide in the disinfecting liquid.

The commonly used hydrogen peroxide solution contains 3% $H_2O_2$. A wide range of tests has shown that the best effect of the disinfecting system is obtained by using such a concentration of hydrogen peroxide of 3% for at least 20 minutes.

Palatinates are for instance used as catalyst for neutralizing the hydrogen peroxide. The used 3% hydrogen peroxide solution is, however, neutralized by the known systems down to 1% already during the first 1 to 2 minutes, which is unsatisfying for obtaining a good disinfecting effect.

Another problem is found in the fact that the neutralization of the hydrogen peroxide according to the catalyst principle goes very slowly in connection with the very low concentrations with the unfortunate result that small amounts of hydrogen peroxide may remain in the contact lenses, i.e. concentrations being so high that they can irritate the eyes.

U.S. Pat. No. 5,089,240 discloses an appliance of the above type for disinfecting contact lenses. The appliance disclosed by this U.S. patent involves the use of a catalytic element consisting of two elements in order to remedy the above problems.

The first catalytic element is most active in the initially very high concentration of $H_2O_2$. The material composition of this first element described in greater detail in the description can delay the neutralizing speed slightly with the result that 1% of $H_2O_2$ still remains in the solution after a neutralization for 30 minutes of a starting concentration of 3% $H_2O_2$.

This first catalytic element ceases to have an effect after 80 to 90 minutes at an $H_2O_2$-concentration of approximately 100 ppm. Unlike this first catalytic element, the second catalytic element is primarily effective at lower $H_2O_2$-concentrations, such as 300 ppm, due to its material composition, and it continues its neutralizing effect in such a manner that an $H_2O_2$-concentration of less than 15 ppm is in fact obtained within 6 hours, which is indicated to be a concentration not irritating the eye.

BRIEF DESCRIPTION OF THE INVENTION

The object of the invention is to provide an apparatus which also assists in maintaining a high $H_2O_2$-concentration for 20 minutes, and which subsequently assists in neutralizing the $H_2O_2$-solution down to such a low value that the remaining amount of $H_2O_2$ on contact lenses does not irritate the eyes.

This object is according to the invention solved by the subject matter of the characterising clause of claim 1.

The oxygen released during the neutralization of $H_2O_2$ is collected below the lamellas and retained for a short period of time on the surface of the catalyst, whereby it blocks up the access of $H_2O_2$. The neutralization of $H_2O_2$ goes slowly in this phase due to the $O_2$-blocking of the surface of the catalyst.

When the concentration of $H_2O_2$ nevertheless drops after a suitable period of time which suffices for obtaining a good disinfection, the release of $O_2$ from the $H_2O_2$-solution is gradually slowed down in such a manner that the $O_2$-blocking of the surface of the catalyst finally ceases. Now the catalyst is freely accessible for the $H_2O_2$-solution in such a manner that the neutralization of the remaining $H_2O_2$-concentration is accelerated relative to the previous phase involving the $O_2$-blocking of the surface of the catalyst. During this second phase, a large catalyst surface is free for the neutralization of the remaining hydrogen peroxide.

Claim 2 deals with an advantageous embodiment according to the invention, as the oxygen is collected in the downwardly facing air pockets between the bottom sides of the spokes and the surface of the catalyst, and as said oxygen only slowly escapes through the small apertures.

Claim 3 deals with an embodiment allowing the developed oxygen to slowly rise along the helical winding.

Several small apertures can be provided for the escape of the oxygen from the helical winding, but only one winding is necessary at the top of the winding as stated in claim 4.

BRIEF DESCRIPTION OF THE DRAWING

The invention is explained in greater detail below with reference to the accompanying drawing, in which.

BEST MODE FOR CARRYING OUT THE INVENTION

Figure 2:
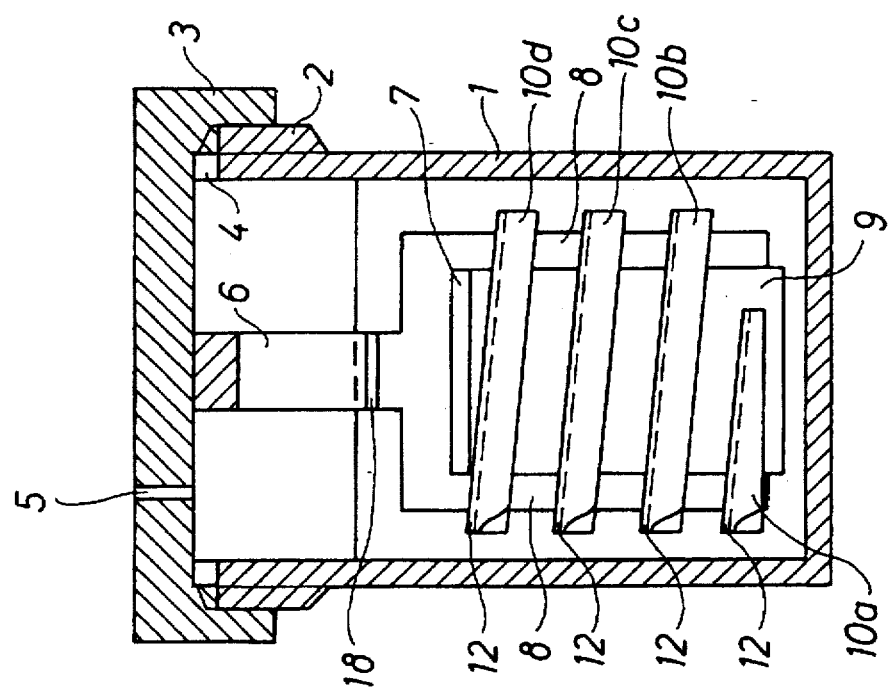
FIG. 2 is a sectional view taken along the line II—II of FIG. 1.

The corresponding parts have the same reference numerals in the drawing.

The apparatus shown in the Figures of the drawing comprises a cylindrical reaction vessel 1, onto which a cover 3 can be screwed by means of a threaded connection 2. A gasket 4 is provided between the reaction vessel 1 and the bottom side of the cover 3. As illustrated in FIG. 2, the cover comprises an air-escape opening 5, but instead of this opening 5 the gasket 4 can be shaped in such a manner that it allows a ventilation from the interior of the reaction vessel.

A frame 6 is secured to the bottom side of the cover. In the illustrated embodiment this frame is formed as a two-pronged fork, whereby a catalytic element 9 is inserted in a compartment 7 between the legs 8 of said fork. The catalytic element is retained by way of friction both between the legs 8 of the frame and between the walls of the compartment 7. The walls comprise apertured lamellas 10a to 10h.

Figure 1:
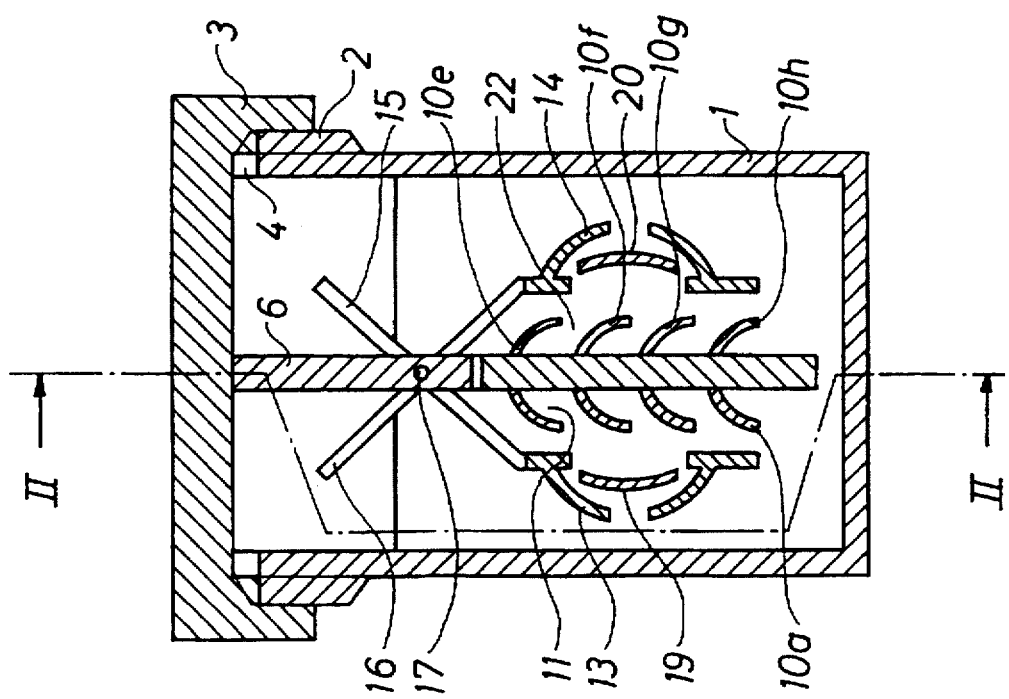
FIG. 1 is a cross-sectional view through a first embodiment according to the invention.

These lamellas extend obliquely downwards away from the surface of the catalytic element in such a manner that four lamellas are provided on each side of the compartment 7, cf: FIG. 1. The number of lamellas is, however, not decisive and can be determined according to desire. As shown in FIG. 1, the lamellas are curved, but they may also be plane. As previously mentioned, the shown lamellas are inclining downwards away from the catalytic element, and in addition the lamellas incline relative to horizontal, cf. FIG. 2. It should be stated that the lamellas can be arranged perpendicular to the surface of the catalytic element or even be slightly upwardly inclined, such as 5°, in a direction away from the catalytic surface. In addition, when seen in the longitudinal direction the lamellas can be horizontal unlike the lamellas shown in FIG. 2.

As shown in FIG. 1, a downward air pocket 11 can be provided below each lamella, and this air pocket ends in small apertures 12, cf. FIG. 2, in the uppermost end of each lamella 10a to 10h in the use position.

A set of basket or net-like lens holders 13, 14 can furthermore be secured to the frame. These lens holders are secured to their respective two-armed lever 15; 16 which are pivotally mounted about a shaft pivot 17 through an opening 18 in the end of the frame 6 provided above the legs 8.

It should be noted that these basket or net-like lens holders 13, 14 as well as their securing to the frame have not been shown in FIG. 2 for the sake of clarity.

The basket or net-like lens holders 13, 14 contain a pair of contact lenses 19, 20, respectively. The lens holders 13, 14 are retained in the position shown in FIG. 1 by the force of a spring means not shown, but conventionally known. The lens holders 13, 14 can be opened by the free ends of the levers 15, 16 being pressed towards one another against the force of the spring means.

When the apparatus is to be used, the reaction vessel 1 is filled with a 3% solution of hydrogen peroxide $H_2O_2$ up to the surface 21 shown. The contact lenses 19, 20 are placed in the lens holders 13, 14 and immersed into the reaction vessel 1 with the $H_2O_2$-solution, whereafter the cover 3 is screwed on the reaction vessel 1.

Now the catalyst 9 neutralizes the $H_2O_2$-solution, said solution being contacted with the catalyst 9 through the access apertures 22. The neutralization goes on, however, very slowly at first because already during the first few seconds oxygen develops vigorously, said oxygen being collected in the air pockets 11 and covering the surface of the catalyst 9. In this manner an $O_2$-blocking layer is formed on the surface of the catalyst, and this blocking layer delays the neutralization of the $H_2O_2$-solution in the reaction vessel 1.

The oxygen confined in the air pockets 11 escapes gradually through the small apertures 12 in each spoke. The oxygen rises to the surface 21 and escapes from the vessel through the outlet opening 5 or optionally through the gasket 4 provided said gasket has been made oxygen-permeable.

After a suitable period sufficient for obtaining a good disinfecting effect of the contact lenses 19, 20, the concentration of $H_2O_2$ has dropped so much that the $O_2$-blocking of the surface of the catalyst gradually ceases. In this manner the catalyst becomes free with the result that the neutralization of the remaining concentration of $H_2O_2$ is accelerated. Subsequently, the process continues until the $H_2O_2$-concentration is sufficiently low and the remaining concentration in the contact lenses 19, 20 does not irritate the eyes.

Figure 4:
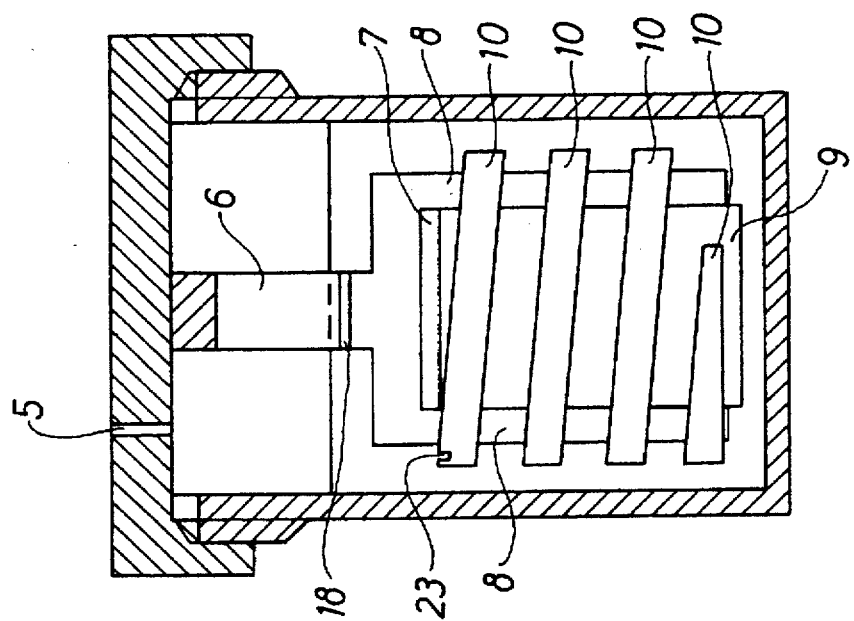
FIG. 4 is a sectional view taken along the line IV—IV of FIG. 3.
Figure 3:
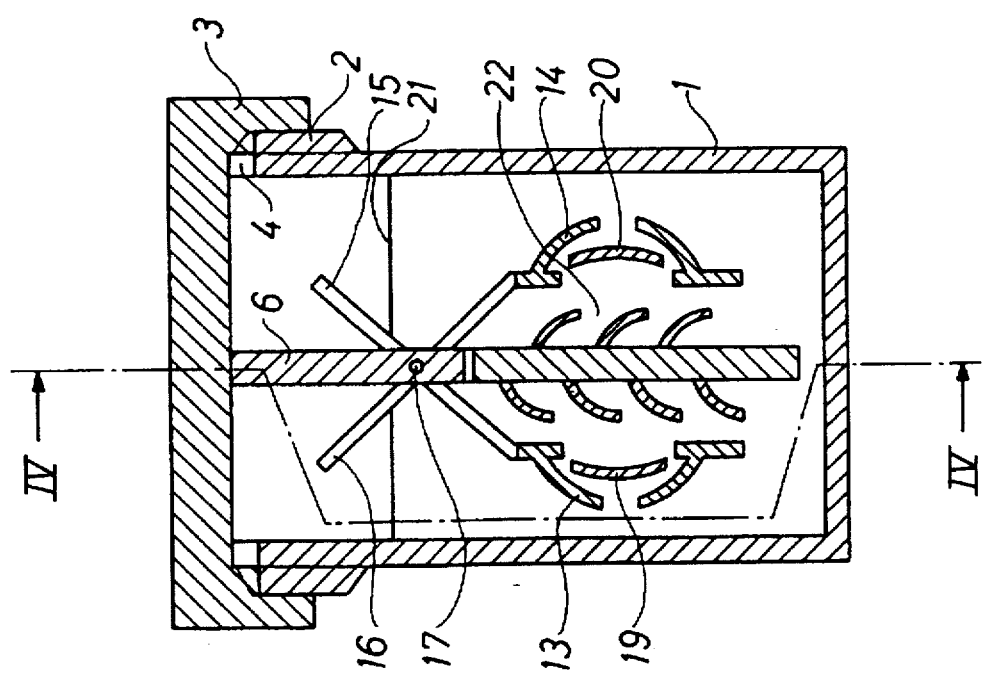
FIG. 3 is a cross-sectional view through a second embodiment according to the invention.

The embodiment of FIGS. 3 and 4 differs only from the first embodiment of FIGS. 1 and 2 by the spokes 10a to 10h being interconnected and extending as a helical winding 10 rising along an axis which is vertical in the use position. This helical winding 10 completely surrounds the catalytic element 9.

Therefore the oxygen, $O_2$, developed rises along the helical winding 10 and escapes through a small opening 23 positioned in the uppermost end of the helical winding 10. Subsequently, the oxygen rises in the same manner as stated above to the $H_2O_2$-surface and escapes through the ventilating opening 5 or optionally through the gasket 4.

I claim:

1. In an apparatus for disinfecting contact lenses comprising a reaction vessel for immersing said lenses with disinfecting liquid in form of a hydrogen peroxide solution $H_2O_2$ having basket or net-like holders in which the contact lenses are placed on a frame also having a compartment walls provided with inlet openings for the $H_2O_2$-solution, and comprising a catalytic element for gradually decomposing the $H_2O_2$-concentration over a period of time, the improvement comprising the walls of the compartment having a system of lamellas abutting the catalytic element and extending away from said element, forming means such that the oxygen, $O_2$, developed during the decomposition of the $H_2O_2$-concentration is collected below said lamellas and maintained in contact with the catalytic element; and said lamellas comprising aperture means to permit the escape of collected oxygen.

2. An apparatus as claimed in claim 1, wherein the lamellas are downwardly inclining away from the catalytic element to form downwardly facing air pockets, and have one or more small apertures for the slow escape of the oxygen.

3. An apparatus as claimed in claim 2, wherein the lamellas are interconnected and extend as a helical winding rising along a vertical axis in the use position, said helical winding surrounding the catalytic element.

4. An apparatus as claimed in claim 3, wherein the end of the helical winding uppermost in the use position is provided with said small aperture through which the oxygen slowly escapes.

\* \* \* \* \*